(12) United States Patent
Kamath et al.

(10) Patent No.: US 8,252,330 B2
(45) Date of Patent: Aug. 28, 2012

(54) TABLET CONTAINING COATED PARTICLES OF CETIRIZINE, PSEUDOEPHEDRINE, AND/OR NAPROXEN

(75) Inventors: Satish Kamath, Mason, OH (US); Michael Nichols, Somerset, NJ (US)

(73) Assignee: McNEIL-PPC, Inc., Skillman, NJ (US)

( * ) Notice: Subject to any disclaimer, the term of this patent is extended or adjusted under 35 U.S.C. 154(b) by 195 days.

(21) Appl. No.: 12/651,495

(22) Filed: Jan. 4, 2010

(65) Prior Publication Data
US 2010/0172980 A1  Jul. 8, 2010

Related U.S. Application Data

(60) Provisional application No. 61/142,425, filed on Jan. 5, 2009.

(51) Int. Cl.
*A61K 9/24* (2006.01)

(52) U.S. Cl. .......... 424/472; 424/469; 514/255.04; 514/569; 514/646; 514/724; 514/730; 514/740; 514/741

(58) Field of Classification Search .......... 424/469, 424/472; 514/255.04, 569, 514, 646, 724, 514/730, 740, 741
See application file for complete search history.

(56) References Cited

U.S. PATENT DOCUMENTS

| | | |
|---|---|---|
| 5,215,755 A | 6/1993 | Roche et al. |
| 5,817,340 A | 10/1998 | Roche et al. |
| 6,051,585 A | 4/2000 | Weinstein et al. |
| 6,171,618 B1 | 1/2001 | Johnson et al. |
| 6,469,009 B1 | 10/2002 | Van De Venne et al. |
| 6,489,329 B2 | 12/2002 | Van De Venne et al. |
| 6,537,573 B2 | 3/2003 | Johnson et al. |
| 6,613,357 B2 | 9/2003 | Faour et al. |
| 6,767,200 B2 | 7/2004 | Sowden et al. |
| 6,780,435 B2 | 8/2004 | Chen et al. |
| 6,814,979 B2 | 11/2004 | Rudnic et al. |
| 7,014,867 B2 * | 3/2006 | Fanara et al. .......... 424/472 |
| 7,217,429 B2 | 5/2007 | Garcia et al. |
| 7,226,614 B2 | 6/2007 | Fanara et al. |
| 7,332,183 B2 | 2/2008 | Plachetka et al. |
| 7,488,497 B2 | 2/2009 | Depui et al. |
| 2002/0119196 A1 * | 8/2002 | Parikh et al. .......... 424/472 |
| 2003/0069255 A1 | 4/2003 | Plachetka |
| 2003/0109453 A1 | 6/2003 | Catania et al. |
| 2004/0156902 A1 | 8/2004 | Lee et al. |
| 2004/0253311 A1 | 12/2004 | Berlin et al. |
| 2005/0249799 A1 | 11/2005 | Jacob et al. |
| 2006/0057205 A1 | 3/2006 | Srinivasan |
| 2006/0240105 A1 | 10/2006 | Devane et al. |
| 2010/0172985 A1 | 7/2010 | Kamath et al. |
| 2010/0172987 A1 | 7/2010 | Kamath et al. |

FOREIGN PATENT DOCUMENTS

| | | |
|---|---|---|
| EP | 0348683 A1 | 1/1990 |
| EP | 1392241 B1 | 7/2009 |
| WO | WO 99/15173 A1 | 4/1999 |
| WO | WO 2004/056320 A2 | 7/2004 |
| WO | WO 2005/120465 A2 | 12/2005 |
| WO | WO-2005/120465 A2 * | 12/2005 |
| WO | WO 2007/021968 A2 | 2/2007 |

OTHER PUBLICATIONS

International Search Report dated Mar. 3, 2010 for PCT/US2010/020023.
Dinç et al., "Chemometric determination of naproxen sodium and pseudoephedrine hydrochloride in tablets by HPLC," Chem Pharm Bull (Tokyo) Apr. 2006; 54(4):415-21.
Ekpe et al., "High-Performance Liquid Chromatographic Method Development and Validation for the Simultaneous Quantitation of Naproxen Sodium and Pseudoephedrine Hydrochloride Impurities," J Chromatogr Sci. Mar. 2001;39(3):81-6.
Fiesco et al., "Bioequivalence study of a new combination of naproxen sodium plus pseudoephedrine capsules in a Mexican sample population," Proc West Pharmacol Soc. 1994;37:161-2.
Gallardo et al., "Symptomatic treatment of common cold in children with a new combination of naproxen sodium plus pseudoephedrine hydrochloride: a comparative trial against pseudoephedrine syrup", Proc West Pharmacol Soc. 1994; 37:161-2.
Leiberman et al., "Pharmaceutical Dosage Forms—Tablets," vol. 3, Chapter 3: "Particle Coating Methods," 1990.
Gupta,P.K., Remington: The Science and Practice of Pharmacy, "Solutions and Phase Equilibria," Chapter 16, pp. 208-226, 2000.

* cited by examiner

*Primary Examiner* — Fereydoun G Sajjadi
*Assistant Examiner* — Ali Soroush
(74) *Attorney, Agent, or Firm* — William E. McGowan

(57) ABSTRACT

In one aspect, the present invention features a tablet including a first drug layer and a second drug layer, wherein: (i) the first drug layer includes first drug particles including naproxen and third drug particles including cetirizine, where the first drug particles and/or the third drug particles are coated with an immediate release coating; and (ii) the second drug layer including pseudoephedrine, wherein said second drug layer is a sustained release layer adapted to deliver a therapeutically effective amount of pseudoephedrine for a period of at least twelve hours.

20 Claims, No Drawings

TABLET CONTAINING COATED PARTICLES OF CETIRIZINE, PSEUDOEPHEDRINE, AND/OR NAPROXEN

CROSS REFERENCE TO RELATED APPLICATIONS

This application claims benefit of U.S. Provisional Application No. 61/142,425 filed Jan. 5, 2009. The complete disclosure of the aforementioned related U.S. patent application is hereby incorporated herein by reference for all purposes.

BACKGROUND OF THE INVENTION

Many upper respiratory allergy sufferers also suffer nasal congestion and headaches or other associated pains. Thus, there is a need for a product that can treat all three of these symptoms, preferably a single tablet that can treat such symptoms for over a period of eight hours. However, combining pharmaceutically active agents into a single tablet often creates difficulties. First, the duration of action for pharmaceutically active agents are often different, and thus, extended release of one or more of the pharmaceutically active agents may be required. Also, pharmaceutically active agents may be incompatible in that they react and degrade when combined with each other.

Both of these issues exist with the combination of the antihistamine cetirizine, the nasal decongestant pseudoephedrine, and the analgesic naproxen. While naproxen is approved for use up to twelve hours and cetirizine is approved for up to twenty-four hours (both without extended release modifications), pseudoephedrine is not. Also, applicants have discovered that cetirizine degrades in the physical presence of both pseudoephedrine and naproxen when combined in a tablet.

Thus, the present invention relates to a novel tablet that contains these three pharmaceutically active agents.

SUMMARY OF THE INVENTION

In one aspect, the present invention features a tablet including a first drug layer and a second drug layer, wherein: (i) the first drug layer includes first drug particles including naproxen and third drug particles including cetirizine, where the first drug particles and/or the third drug particles are coated with an immediate release coating; and (ii) the second drug layer including a decongestant (e.g., pseudoephedrine), wherein said second drug layer is a sustained release layer adapted to deliver a therapeutically effective amount of the decongestant for a period of at least four hours (e.g., at least twelve hours).

In another aspect, the present invention features a method of manufacturing a tablet, wherein the method includes: (i) preparing the first drug particles including naproxen utilizing a granulation process; (ii) preparing a second powder mixture including a decongestant utilizing a dry blending or granulation process; (iii) preparing the third drug particles including cetirizine utilizing a layering or granulation process; (iv) coating the first drug particles and/or the third drug particles with an immediate release coating; (v) blending the first drug particles and the second drug particles to form a first drug blend; (vi) compressing the first drug blend to form the first drug layer; and (vii) compressing the first drug layer and the second drug particles to form the tablet.

In another aspect, the present invention features a method of treating symptoms of upper respiratory allergies, nasal congestion, and headache (e.g., for at least for at least twelve hours) by administering a tablet including naproxen, cetirizine, and a decongestant to a person in need to such treatment.

In another aspect, the present invention features a tablet including a first drug particles including naproxen, second drug particles including a decongestant, and third drug particles including cetirizine, wherein (i) the first drug particles and/or the second drug particles are coated with an immediate release coating and (ii) wherein said second drug layer is a sustained release layer adapted to deliver a therapeutically effective amount of the decongestant for a period of at least four hours (e.g., at least twelve hours).

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

"Water soluble," as used herein in connection with non-polymeric materials, shall mean from sparingly soluble to very soluble, i.e., not more than 100 parts water required to dissolve 1 part of the non-polymeric, water soluble solute. See Remington, The Science and Practice of Pharmacy, pp 208-209 (2000). "Water soluble," as used herein in connection with polymeric materials, shall mean that the polymer swells in water and can be dispersed at the molecular level or dissolved in water. "Water swellable," as used herein in connection with polymeric materials, shall mean that the polymer swells in water but is not dispersed at the molecular level or dissolved in water.

"Modified release" as used herein refers to the release rate for the pharmaceutically active agent from the tablet or drug layer other than immediate release, including but not limited to sustained, pulsatile, and enteric release.

As used herein, the term "substantially covers" means covering at least 50%, such as at least 75%, such as at least 90%, such as at least 95%, such as at least 99% of a surface.

As used herein, the term "substantially free" means less than 0.1 percent by weight, such as less than 0.01 percent by weight, such as less that 0.001 percent by weight, such as 0 percent by weight.

"Therapeutically effective amount," as used herein, is an amount of a pharmaceutically active agent that produces the desired therapeutic response upon oral administration. One skilled in the art can readily determine the therapeutically effective amount (e.g., effective blood levels) of a pharmaceutically active agent for a given patient by considering factors such as, for example, the particular pharmaceutically active agent being administered; the bioavailability characteristics of the pharmaceutically active agent; the dose regimen desired; the age and weight of the patient; and the like.

Pharmaceutically Active Agents

In one embodiment, the tablets of the present invention contains the pharmaceutically active agents cetirizine, pseudoephedrine, and naproxen. The term "cetirizine" includes isomers thereof (such as levocetirizine) and pharmaceutically acceptable salts (such as cetirizine dihydrochloride and levocetirizine dihydrochloride). The term "pseudoephedrine" includes pharmaceutically acceptable salts thereof (such as pseudoephedrine HCl). The term "naproxen" includes pharmaceutically acceptable salts thereof (such as naproxen sodium).

In one embodiment, the tablet contains another decongestant (such as phenylephrine) rather then pseudoephedrine. The term "phenylephrine" includes pharmaceutically acceptable salts thereof (such as phenylephrine HCl).

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

In one embodiment, the pharmaceutically active agent or agents are present in the tablet in a therapeutically effective amount. In one embodiment, the tablet (e.g., the first drug layer) contains from about 200 to about 250 mg of naproxen sodium; the tablet (e.g., the second drug layer) contains from about 100 to about 150 mg of pseudoephedrine HCl; and the tablet (e.g., the first drug layer) contains from about 4 to about 6 mg of cetirizine dihydrochloride (i.e., cetirizine HCl).

Fluid Bed Granulation of First Powder Mixtures and Third Powder Mixture

In one embodiment, the first powder mixture containing naproxen (used to manufacture the first drug layer of the tablet) is prepared by granulation. In one embodiment, the third powder mixture containing cetirizine (used to manufacture the third drug layer of the tablet) is prepared by granulation. Suitable granulation techniques include, but are not limited to, high shear, fluid bed granulation, roller compaction, and chilsonation.

In one embodiment, the first powder mixture is prepared as a direct compression blend and does not undergo a granulation processing step. In one embodiment, the third powder mixture is prepared as a direct compression blend and does not undergo a granulation processing step.

In one embodiment, the amount of naproxen present in the first powder mixture is from about 30 percent to about 90 percent by weight of the first powder mixture, such as from about 40 percent to about 70 percent.

In one embodiment, the amount of cetirizine present in the third powder mixture is from about 5 percent to about 30 percent by weight of the third powder mixture, such as from about 6 percent to about 20 percent.

The first powder mixture and the second powered mixture may further include other tableting excipients such as fillers, glidants, tablet binders, lubricants, disintegrants and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof.

Suitable glidants include, but are not limited to, colloidal silicon dioxide.

Suitable tablet binders include, but are not limited to, hydroxypropyl cellulose, microcrystalline wax, carnuba wax, and mixtures thereof.

Suitable lubricants include, but are not limited to, long chain fatty acids and their salts, such as magnesium stearate and stearic acid, talc, glycerides waxes, and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof. In one embodiment, the powder mixture contains up to about 5 percent by weight of such disintegrant.

Preparation of First and Second Drug Particles with Immediate Release Coating

In one embodiment, the third drug particles are coated with an immediate release coating. In this embodiment, the coated third drug particles a further blended with the first drug particles (that may or may not also have an immediate release coating) and compressed into a first tablet layer.

In one embodiment, the first drug particles are coated with an immediate release coating. In this embodiment, the coated first drug particles a further blended with the third drug particles (that may or may not also have an immediate release coating) and compressed into a first drug layer.

The core of the first drug particles and the second drug particles may be present in a variety of forms. The core active may be present as a pure drug crystal, as a granulated particle, or as a layered particle. In the case of a layered particle, the pharmaceutically active agent is layered on to an inert substrate prior to coating with the immediate release coating. Suitable materials for the inert substrate include, but are not limited to: starches, such as corn starch; sugars such as sucrose, lactose, dextrose, mannose, or fructose; sugar alcohols such as mannitol, sorbitol, xylitol, or lactitol; maltodextrin; or celluloses such as microcrystalline cellulose. In certain embodiments, the pharmaceutically active agent is dissolved or suspended in a solvent and layered onto the inert substrate by a spraying process. Useful solvents include, but are not limited to: organic solvents such as acetone, methanol, ethanol, isopropanol; aqueous solvents such as water; and mixtures thereof. In certain embodiments, a polymeric binder is added to the layering solution or suspension and applied to the inert substrate by a spraying process. Suitable polymeric binders include, but are not limited to, polyvinylpyrrolidone, hypromellose, hydroxypropylcellulose, methylcellulose, and polymethacrylates.

In certain embodiments, the pharmaceutically active agent is subjected to a granulation process prior to coating of the particulates with the immediate release coating. Suitable granulation techniques include, but are not limited to, high shear, fluid bed granulation, roller compaction, and chilsonation.

In one embodiment, the immediate release coating substantially covers the third drug particles. In one embodiment, the immediate release coating substantially covers the first drug particles. In one embodiment, the immediate release coating substantially covers both the first drug particles and the third drug particles.

In certain embodiments, a binder is added to the pharmaceutically active agent in order to increase the particle size of the particles. Suitable binders include those listed above as polymeric binders and also include sugars and starches. In one embodiment, the particle size of the particles is from about 30 microns to about 500 microns, such as from about 100 microns to about 350 microns prior to the application of the immediate release coating.

The core of the particle may include pure, crystalline pharmaceutically active agent, or a mixture of pharmaceutically active agent with optional ingredients, such as binders, surfactants, flavorants, sweeteners, release modifying agents, and other excipients known in the art. Suitable release modifying agents include but are not limited to polymers such as hypromellose, cellulose acetate, ethylcellulose, hydroxypropylcellulose, polyethylene oxides, and polymethacrylates.

In embodiments wherein an immediate release coating is added to the drug particle, a variety of materials can be used to produce the immediate release coating. In one embodiment, the immediate release coating contains a water soluble polymer. Suitable water soluble polymers include but are not limited to hypromellose, hydroxypropylcellulose, methylcellulose, starch, polymethacrylates and modified starch. In one embodiment the immediate release coating contains a combination of an insoluble polymer and a soluble polymer. Suitable insoluble non-pH dependent polymers for use in the immediate release coating include but are not limited to ethylcellulose, cellulose acetate, and copolymers of methacrylic acid esters (e.g., ethylacrylate methylmethacrylate copolymers available from Rohm Pharma under the tradename, "Eudragit® NE 30D").

In certain embodiments, pH dependent polymers such as enteric polymers may be included in the immediate release coating. Suitable pH dependent polymers include reverse-enteric polymers such as but not limited to: cationic polymer of methacrylic acid and methacrylates with carboxylic acid functional groups available from Rohm Pharma under the tradename Eudgragit® E100; enteric polymers such as cellulose acetate phthalate, hypromellose phthalate, shellac, zein, hypromellose succinate; and anionic polymers of methacrylic acid and methacrylates which dissolve at a pH 5.5 and above (Eudragit® L 100-55) a 30% dispersion of methylmethacrylate-methacrylic acid copolymers having a carboxylic acid group (Eudragit® L 30), methylmethacrylate-methacrylic acid copolymers having a carboxylic acid group (Eudragit® L 100), and the anionic copolymer of methacrylic acid with carboxylic acid groups (Eudragit® S100). In one embodiment, the enteric polymer may be includes at a level of up to about 50 percent by weight of the immediate release coating.

In one embodiment, a plasticizer is incorporated into the immediate release coating. Example of suitable plasticizers include, but are not limited to polyethylene glycol; propylene glycol; glycerin; sorbitol; triethyl citrate; tributyl citrate; dibutyl sebecate; vegetable oils such as castor oil, rape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glyceroltributyrate; hydrogenated castor oil; fatty acids; substituted triglycerides and glycerides; and the like and/or mixtures thereof. The plasticizer may be present at a level of about 1 percent to about 40 percent, e.g. from about 2 percent to about 20 percent, by weight of the immediate release coating.

In another embodiment, the immediate release coating includes, based upon the total weight of the coated particle, from about 1 percent to about 40 percent, such as from about 2 percent to about 25 percent, of the immediate release coating.

The mean particle size of coated particles, including the pharmaceutically active agent and the immediate release coating, may range from about 30 to about 1000 microns, such as from about 50 microns to 600 microns or from about 100 microns to about 400 microns.

Optional ingredients well known in the art may also be added to the composition suitable for use in the immediate release coating. Examples of such optional ingredients include, but are not limited to: fillers, including water soluble compressible carbohydrates such as sucrose, mannitol, sorbitol, maltitol, xylitol, erythritol, lactose, and mixtures thereof; polymers including gelatin, gellan gum, xanthan gum, locust bean gum, carrageenan, polyvinyl acetate, polyvinyl alcohol, polyvinyl pyrrolidone, starch, modified starch, maltodextrin, and mixtures thereof, and in particular microcrystalline cellulose, maltodextrin, and starch; sweeteners including aspartame, acesulfame potassium, sucralose and saccharin; disintegrants such as microcrystalline cellulose, starch, sodium starch glycolate, cross linked polyvinylpyrrolidone, cross linked carboxymethylcellulose; preservatives, flavors, acidulants, antioxidants, glidants, surfactants, and coloring agents. Any of the optional ingredients set forth above are also suitable for use in second coating layer. Typically, the amount of optional ingredients in the composition suitable for use in either the first coating layer or the second coating layer is, based upon the total wet weight of each respective composition, from about 1 percent to about 40 percent.

Suitable surfactants include both ionic and non-ionic materials from both synthetic and natural origins, including but not limited to lecithin, glyceryl esters, sugar esters, polysorbates, mono and diglycerides of fatty acids, propylene glycol esters, sucrose fatty acid esters, polyoxyethylene derivatives of sorbitan fatty acid esters, and mixtures thereof. Examples of useful polysorbates include sorbitan trioleate, sorbitan monopalmitate, sorbitan monolaurate, propylene glycol monolaurate, glycerol monostearate, diglycerol monostearate, glycerol lactyl-palmitate. Lactic acid derivatives include sodium stearoyl lactylate and calcium stearoyl lactylate. In one embodiment, when a surfactant is present in the first coating layer, the level of surfactant is present in an amount, based upon the total weight of the first coating layer, from about 2 percent to about 10 percent.

The immediate release coating may be applied to the particle core in the form of a solution using fluidized bed technology, such as Wurster coating or rotor coating. Useful solvents include, but are not limited to, acetone, methanol, ethanol, isopropanol; aqueous solvents such as water; and mixtures thereof. One suitable solvent mixture includes acetone and water at a ratio from about 85:15 to about 95:5. In one embodiment, the pharmaceutically active agent particle including the immediate release coating is prepared by microencapsulation techniques such as coaccervation or complex coaccervation. In one embodiment the pharmaceutically active agent particle including the immediate release coating is prepared according to spray drying or spray congealing.

In one embodiment, the immediate release coating is applied by a fluidized bed process wherein a melted coating is applied to the particle.

In one embodiment, the thickness of the immediate release coating is from about 1 micron to about 20 microns, such as from about 2 microns to about 15 microns, such as from about 4 to about 9 microns.

In one embodiment, the immediate release coating is present in an amount, based upon the total weight of the coated particle before the addition of any second coating thereto, from about 5 percent to about 50 percent, such as from about 15 percent to about 25 percent.

One skilled in the art may readily appreciate that the coating conditions, such as solution spray rate, drying air temperature, and flow rate must be adjusted in order to achieve an equilibrium between the rate of application of the liquid coating solution, and the rate of evaporation of the solvents such that the immediate release coating can be deposited uniformly on the particle to form a complete film without over-wetting the particle surface. Details of these methods are well known in the art and set forth in, for example, Lieberman et al., "Pharmaceutical Dosage Forms—Tablets: Volume 3", Chapter 3: Particle Coating Methods (1990), which is incorporated by reference herein.

In one embodiment, suitable low-melting materials for use in immediate release coating include fats, fatty acid esters, phospholipids, and waxes. Examples of suitable fats include hydrogenated vegetable oils such as for example cocoa butter, hydrogenated palm kernel oil, hydrogenated cottonseed oil, hydrogenated sunflower oil, and hydrogenated soybean oil; and free fatty acids and their salts. Examples of suitable fatty acid esters include sucrose fatty acid esters, mono, di, and triglycerides, glyceryl behenate, glyceryl palmitostearate, glyceryl monostearate, glyceryl tristearate, glyceryl trilaurylate, glyceryl myristate, lauroyl macrogol-32 glycerides, and stearoyl macrogol-32 glycerides. Examples of suitable phospholipids include phosphotidyl choline, phosphotidyl serene, phosphotidyl enositol, and phosphotidic acid. Examples of suitable waxes include carnauba wax, spermaceti wax, beeswax, candelilla wax, shellac wax, microcrystalline wax, and paraffin wax.

In one embodiment, the immediate release coating is substantially free of an pharmaceutically active agent. In one embodiment, the immediate release coating is substantially free of cetirizine. In one embodiment, the immediate release immediate release coating is substantially free of a basic compound. Basic compounds include but are not limited to sodium hydroxide, potassium hydroxide, and magnesium stearate.

In one embodiment, a second coating may be placed on the surface of the immediate release coating. The second coating may be applied to improve the taste, texture or release of the cetirizine or naproxen and may include any of the types of coating materials that are described for the immediate release coating above.

Modified Release Second Powder Mixture Containing a Decongestant

In one embodiment, the decongestant is delivered in a modified release manner through a modified release matrix containing a second powder mixture containing (i) pseudoephedrine and/or another decongestant such as phenylephrine and (ii) a water insoluble modified release excipient. Examples of suitable water-insoluble modified release excipients include, but are not limited to, water-insoluble polymers, water-swellable polymers and low-melting hydrophobic materials, and mixtures thereof. In one embodiment, the modified release matrix is prepared as a dry blend. In another embodiment, the modified release matrix is prepared as a granulation. In another embodiment, the modified release matrix is prepared as a wet granulation which is dried prior to compression. In one embodiment, the decongestant is released in a zero-order manner. In one embodiment, the decongestant is released in a first-order manner.

Examples of suitable water-insoluble polymers include, but are not limited to, water-swellable celluloses (such as hypromellose), polyalkylene glycols, thermoplastic polyalkylene oxides, acrylic polymers and co-polymers, hydrocolloids, swelling cross-linked polymers, and mixtures thereof. Examples of suitable water swellable celluloses include, but are not limited to, hypromellose, sodium carboxymethylcellulose, hydroxypropylcellulose, cross-linked hydroxypropylcellulose, hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols for use in the modified release matrix include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, methacrylic ester copolymers, ammonio methacrylate copolymers (such as those commercially available from Evonik Industries under the under the tradename EUDRAGIT® EL and RS), high-molecular weight cross-linked acrylic acid homopolymers and copolymers (such as those commercially available from Noveon Chemicals under the tradename CARBOPOL™ (e.g., having a viscosity of greater than 50,000 centipoise when tested using a Brookfield RVT Viscometer at 25° C., using spindle #7, when dispersed in a basic solution)). Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof.

Examples off suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, paraffin wax, and mixtures thereof.

In one embodiment, the water insoluble release modifying excipient is the polymer hydroxypropylmethylcellulose, also known as hypromellose (such as those commercially available from the Dow Corporation as Methocel® K3, K4M, K15M, K100M), or hydroxypropyl cellulose (such as those commercially available from Ashland Chemical corporation as Klucel® HXF, HF HPC or Natrosol® HHX or HX HEC), or mixtures thereof.

In one embodiment, the amount of modified release polymer in the second powder mixture is from about 20 percent to about 70 percent, such as from about 35 percent to about 60 percent, by weight of the second powder mixture.

In one embodiment, the second drug layer contains modified release particles of pseudoephedrine and/or another decongestant such as phenylephrine. In one embodiment, the modified release particles are prepared using a modified release coating. In one embodiment, the modified release coating includes at least one modified release polymer such as cellulose acetate, ethylcellulose, or methacrylic polymers, such as those commercially available from Rohm America such as Eudragit® NE-30D, RS, and RL polymers. In one embodiment, the modified release coating further includes a plasticizer. Suitable plasticizers include but are not limited to triethylcitrate, tributyl citrate, propylene glycol, castor oil, and triacetin.

In one embodiment, the amount of pseudoephedrine or other decongestant present in the second powder mixture is from about 10 percent to about 50 percent by weight of the second powder mixture, such as from about 20 percent to about 40 percent.

Modified Release Coated Particle Containing a Decongestant

In one embodiment, the decongestant is delivered in a modified release manner through a coated particle. In one embodiment, the coating is applied to a particle such that the decongestant is delivered over at least 8 hours, such at least 12 hours. Suitable coatings for such use include pH independent polymers such as ethylcellulose, cellulose acetate, and polymethacrylic acid copolymers, such as those commercially available from Rohm America as "Eudragit® RS" and "Eudragit® RL"; copolymers of methacrylic acid esters, such as ethylacrylate methylmethacrylate copolymers available from Rohm Pharma under the tradename Eudragit® NE 30D.

In one embodiment, the preparation of the core decongestant particle prior to the application of the modified release coating is as those described above and include drug layering and granulation. The modified release coating may also be applied using those techniques described above, including fluidized bed coating and microencapsulation. In one embodiment, the coating is applied at a level from about 10 percent to about 70 percent, such as from about 10 percent to about 40 percent by weight of the coated particle including the decongestant. Other materials may also be included in the coating, such as water soluble polymers, plasticizers, glidants such as colloidal silicon dioxide and talc, and surfactants.

Manufacture of Tablet

In one embodiment, the components of the powder are blended together, for example as dry powders, and fed into the die cavity of an apparatus that applies pressure to form a tablet core. Any suitable compacting apparatus may be used, including, but not limited to, conventional unitary or rotary tablet press. In one embodiment, the tablet core may be formed by compaction using a rotary tablet press (e.g., such as those commercially available from Fette America Inc., Rockaway, N.J. or Manesty Machines LTD, Liverpool, UK). In general, a metered volume of powder is filled into a die cavity (where the powder is either gravity fed or mechanically fed from a feeder) of the rotary tablet press, and the cavity rotates as part of a "die table" from the filling position to a compaction position. At the compaction position, the powder is compacted between an upper and a lower punch, then the resulting tablet core is pushed from the die cavity by the lower punch and then guided to an injection chute by a stationary "take-off" bar.

In another embodiment, the tablet may be prepared by the compression methods and apparatus described in U.S. Patent Application Publication No. 20040156902. Specifically, the tablet core may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder recovery system to recover excess powder from the filters and return the powder to the dies.

In one embodiment, the tablet core is prepared by the compression methods and apparatus described in issued U.S. Pat. No. 6,767,200. Specifically, the tablet core is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

The tablet core may have one of a variety of different shapes. For example, the tablet core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet core has one or more major faces. For example, the tablet core surface typically has opposing upper and lower faces formed by contact with the upper and lower punch faces in the compression machine. In such embodiments the tablet core surface typically further includes a "belly-band" located between the upper and lower faces, and formed by contact with the die walls in the compression machine.

In one embodiment the tablet is prepared as a bilayer compressed tablet including the modified release matrix including pseudoephedrine and/or coated modified release coated particles including pseudoephedrine in the second drug layer and the coated third particles and uncoated first drug particles in the first drug layer.

In one embodiment the tablet is prepared as a bilayer compressed tablet including the modified release matrix including pseudoephedrine and/or coated modified release coated particles including pseudoephedrine in the second drug layer and the coated first drug particles and uncoated third drug particles in the first drug layer.

In one embodiment the tablet is prepared as a single layer compressed tablet including the modified release coated pseudoephedrine particles, the coated third drug particles, and uncoated first drug particles.

In one embodiment the tablet is prepared as a single layer compressed tablet including the modified release coated pseudoephedrine particles, the coated first drug particles and uncoated third drug particles.

In one embodiment, the first powder mixture is compressed at forces from about 0.5 kiloNewtons to about 10 kiloNewtons, such as from about 0.5 kiloNewtons to about 2 kiloNewtons, to form the first drug layer; the second powder mixture is compressed with the first drug layer at forces from about 1 kiloNewtons to about 15 kiloNewtons, such as from about 1 kiloNewtons to about 10 kiloNewtons, to form a two layer tablet core.

In one embodiment, each powder mixture has an average particle size if about 50 microns to about 500 microns, such as between 50 microns and 300 microns.

In one embodiment, the amount of pseudoephedrine or other decongestant present in the second drug layer is from about 5 percent to about 50 percent by weight of the second drug layer, such as from about 10 percent to about 40 percent.

In one embodiment, the amount of naproxen present in the first drug layer is from about 30 percent to about 90 percent by weight of the first drug layer, e.g. from about 40 percent to about 70 percent; and the amount of cetirizine present in the first drug layer is from about 5 percent to about 30 percent by weight of the first drug layer, such as from about 6 percent to about 20 percent.

In one embodiment, the amount of p-chlorobenzophenone (p-CBP), a degredant of cetirizine, present in the tablet (i.e., if any) is less than 0.2%, such as less than 0.1%, such as less than 0.05%, by weight of the amount of cetirizine in the tablet following storage of the tablet at 40 degrees Celsius and 75 percent relative humidity for at least 3 months.

Film Coating Tablet

In one embodiment, the tablet core (e.g., the first drug layer and the second drug layer,) is coated with a protective film coating. In one embodiment, the film coating does not contain a pharmaceutically active agent. In one embodiment, the film coating contains a film-forming polymer that is water-soluble. Examples of suitable water-soluble film forming polymers include, but are not limited to, hypromellose, starch, modified starch, hydroxypropyl cellulose, methylcellulose, polyvinyl alcohol and polyvinyl alcohol and polyethylene glycol copolymers. In one embodiment, the amount of the coating layer is from about 0.5 percent to about 8 percent, such as from about 1 percent to about 5 percent by weight of the coated tablet.

Use of Tablet

In one embodiment, the present invention features a method of treating symptoms of upper respiratory allergies including seasonal allergies and rhinitis (such as due to hay fever) and situational allergies (such as dust and pet allergies), nasal congestion (including sinus congestion), and headache (such as sinus headache) by administering a tablet of the present invention to a person in need to such treatment. Examples of symptoms of upper respiratory allergies include, but are not limited to, runny nose, sneezing, itchy/watery eyes, and itching of the nose or throat.

In one embodiment, the tablet is adapted to maintain a therapeutically effective amount of pseudoephedrine for a period of at least four hours upon ingestion, such as at least eight hours upon ingestion, such as at least twelve hours upon ingestion, such as at least twenty-four hours upon ingestion.

EXAMPLES

Specific embodiments of the present invention are illustrated by way of the following examples. This invention is not confined to the specific limitations set forth in these examples.

Example 1

Preparation of Granulation (for Coating) Containing Naproxen Sodium

The naproxen sodium, first quantity of croscarmellose sodium and microcrystalline cellulose from Table 1 are placed into a Glatt GPCG 15 fluid bed granulator (commercially available from Glatt Air Techniques in Ramsey, N.J.) equipped with a top-spray insert.

The granulating solution is prepared by adding hydroxypropyl cellulose to 10 kg of purified water and mixed at 100 RPM for approximately 30 minutes. The solution is allowed to cool to approximately 30° C.

The granulating solution is sprayed on to the naproxen blend at a spray rate of 60-120 g/minute at a product temperature of approximately 15-25° C., and dried to a final moisture of less than 5.0% when analyzed using a Computrac® MAX® 2000XL loss on drying moisture analyzer (commercially available from Arizona Instrument LLC in Chandler, Ariz.) set at 100° C. The dried granules are screened through a Glatt Quick Sieve equipped with a 1.5 mm screen.

TABLE 1

Naproxen Granulation Formulation

| Material | Mg/tablet | g/Batch (3518 g) | % Weight in Granulation |
|---|---|---|---|
| Naproxen Sodium USP | 220.00 | 2330 | 68.75 |
| Microcrystalline Cellulose NF[1] (Avicel ™ pH 101) | 80.00 | 848 | 25.00 |
| Croscarmellose Sodium | 4.00 | 170 | 1.25 |
| Hydroxypropyl Cellulose[2] | 16.00 | 170 | 5.00 |
| Purified Water[3] | N/A | N/A | N/A |
| TOTAL | 320.0 | 3518 | 100.0 |

[1]Commercially available from FMC Corporation in Philadelphia, PA as Avicel ™ pH 101
[2]Commercially available from Ashland Inc in Wilmington, DE as Klucel EF ™
[3]Purified water removed from formulation upon drying Example 2

Preparation of Granulation (for Coating) Containing Cetirizine HCl

The microcrystalline cellulose and corn starch from Table 2 are placed into a Glatt GPCG 15 fluid bed granulator equipped with a top-spray insert.

The granulating solution is prepared by adding 10000 g of purified water to a suitable stainless steel vessel and warming to 45° C. The hydroxypropyl cellulose (commercially available as Klucel EF™) is added to purified water and mixed at 100 RPM for approximately 30 minutes. The solution is allowed to cool to approximately 30° C. The cetirizine HCL is then added to the solution and mixed for approximately 15 minutes.

The granulating solution is sprayed on to the microcrystalline cellulose and corn starch blend at a spray rate of 60-120 g/minute at a product temperature of approximately 19-25° C., and dried to a final moisture of less than 4.0% when analyzed using a Computrac® MAX® 2000 XL loss on drying moisture analyzer set at 100° C. The dried granules are screened through a Glatt Quick Sieve equipped with a 1.5 mm screen.

TABLE 2

Cetirizine HCl Granulation Formulation

| Material | Mg/tablet | g/Batch (2824 g batch) | % Weight in Granulation |
|---|---|---|---|
| Cetirizine HCl | 5.00 | 176.5 | 6.25 |
| Microcrystalline Cellulose NF[1] | 50.00 | 1764.7 | 62.50 |
| Corn Starch | 21.00 | 741.2 | 26.25 |
| Hydroxypropyl Cellulose[2] | 4.00 | 141.2 | 5.00 |
| Purified Water[3] | N/A | N/A | N/A |
| TOTAL | 80.0 | 2823.6 | 100.00 |

[1]Commercially available from FMC Corporation in Philadelphia, PA as Avicel ™ pH 101
[2]Commercially available from Ashland Inc in Wilmington, DE as Klucel EF ™
[3]Purified water removed from formulation upon drying

Example 3

Preparation of Controlled Release Pseudoephedrine HCl Blend

Part A: Dry Blend Process

The pseudoephedrine HCl, microcrystalline cellulose, croscarmellose sodium, and colloidal silicon dioxide are passed through a Glatt quick sieve equipped with a 1.5 mm screen. The materials are placed into a 1 cubic foot twin shell 'V' blender and blended for 150-450 revolutions. The magnesium stearate is manually passed through a 20 mesh screen and added to the blend and blended for approximately 100-200 revolutions.

TABLE 3

Pseudoephedrine HCl Blend Formulation

| Material | Mg/tablet | g/Batch | % Weight in Blend |
|---|---|---|---|
| Pseudoephedrine HCl | 120.00 | 2800 | 40.00 |
| Microcrystalline Cellulose NF[1] | 57.00 | 1330 | 19.00 |
| Hypromellose USP[2] | 120.00 | 2800 | 40.00 |
| Colloidal Silicon Dioxide | 1.50 | 35 | 0.50 |
| Magnesium Stearate | 1.50 | 35 | 0.50 |
| TOTAL: | 300.00 | 7000.0 | 100.00 |

[1]Commercially available from FMC Corporation in Philadelphia, PA as Avicel ™ pH 101
[2]Commercially available from Dow Chemical Corporation in Midland Michigan as Methocel K15M CR ™
[3]Purified water removed from formulation upon drying Part B: Pseudoephedrine Granulation Process The sustained release pseudoephedrine layer of Table 3 is manufactured by a granulation process as follows. The pseudoephedrine, hypromellose, and microcrystalline cellulose from Table 3 are placed into a Glatt GPCG 15 fluid bed granulator equipped with a top-spray insert. 2500 g of purified water is sprayed onto to the pseudoephedrine, hypromellose, and microcrystalline cellulose blend at a spray rate of 60-80 g/minute at a product temperature of approximately 19-25° C., and dried to a final moisture of less than 4.0% when analyzed using a Computrac® MAX2000 XL loss on drying moisture analyzer (commercially available from Arizona Instrument LLC in Chandler, Ariz.), set at 100° C. The dried granules are screened through a Glatt Quick Sieve equipped with a 1.5 mm screen. Approximately half of the magnesium stearate and all of the colloidal silicon dioxide are also screened through the Glatt quick sieve equipped with a 1.5 mm screen. The ingredients are blended in a 16 Quart twin shell 'V' Blender for approximately 150-450 revolutions. The remaining magnesium stearate is manually passed through a 20 mesh screen and added to the pseudoephedrine blend in the 'V' Blender, and blended for approximately 100-200 revolutions.

Example 4

Coating of Cetirizine Particles

Part A: Preparation of Protective Coating Solution:

A protective coating solution for cetirizine particles is prepared by slowly adding 425 g of hypromellose (commercially available from Dow Corporation as Methocel™ E-15) and 75 g of triethylcitrate to 5750 g of purified water while mixing at about 50-150 RPM. The solution is allowed to mix for approximately 30 minutes and stand for about 2 hours to allow the foam to dissipate before application. The weight percentage of coating materials in the final coating film are approximately 85 percent hypromellose and 15 percent triethylcitrate, based upon the dried weight of the coating, set forth in Table 4 Below. The percent solids of coating materials in solution is approximately 8 percent.

TABLE 4

Composition of Protective Coating

| Component Name | Amount Present (wt. percent based on dried coating) |
|---|---|
| Hypromellose | 85 percent |
| Triethylcitrate | 15 percent |
| Total | 100 percent |

Part B: Coating of Cetirizine Particles:

Approximately 2000 g of cetirizine granulation from Example 2 is placed into a Glatt Fluid Bed coating unit (GPCG-5/9) equipped with a bottom spray Wurster coating insert and coated using the solution from Part A at a spray rate of approximately 20 g/minute and a product temperature of approximately 28 to 32° C. The final coating particle contains approximately 20 percent of coating.

Example 5

Preparation of Bi-Layer Tablets Containing Controlled Release Pseudoephedrine, Immediate Release Uncoated Naproxen Particles and Immediate Release Coated Cetirizine Particles Part A: Blending of Cetirizine Coated Particles and Naproxen Granulation:

Approximately 277.78 g of coated cetirizine particles from Example 4, Part B and 888.89 g of naproxen granulation from Example 1 are added to a V-Blender and blended end-over end for approximately 10 minutes.

Part B: Compression of Bi-Layer Tablets:

The pseudoephedrine blend from Example 3 and the blended naproxen granulation and cetirizine coated particles from Example 5, Part A are used to compress bi-layer tablets. The tablets are compressed using 0.350×0.710 inches, oval, Standard concave tooling at a compression forces of approx. 20 KN using a KORSCH XL400 rotary tablet press.

TABLE 5

Components of Tablet

| Ingredients | Percent (w/w) | mg/tab |
|---|---|---|
| Controlled Release Pseudoephedrine | 41.7 | 300 |
| Naproxen granulation and Coated Cetirizine | 58.3 | 420 |
| TOTAL | 100.0 | 720 |

Example 6

Coating of Naproxen Sodium Particles

Part A: Preparation of Protective Coating Solution:

A protective coating solution for cetirizine particles is prepared by slowly adding 425 g of hypromellose (commercially available from Dow Corporation as Methocel™ E-15) and 75 g of triethylcitrate to 5750 g of purified water while mixing at about 50-150 RPM. The solution is allowed to mix for approximately 30 minutes and stand for about 2 hours before application. The weight percentage of coating materials in the final coating film are approximately 85 percent hypromellose and 15 percent triethylcitrate, based upon the dried weight of the coating, set forth in Table 6 Below. The percent solids of coating materials in solution is approximately 8 percent.

TABLE 6

Composition of Protective Coating

| Component Name | Amount Present (wt. percent based on dried coating) |
| --- | --- |
| Hypromellose | 85 percent |
| Triethylcitrate | 15 percent |
| TOTAL | 100 percent |

Part B: Coating of Naproxen Sodium Particles:

Approximately 2000 g of naproxen sodium granulation from Example 1 is placed into a Glatt Fluid Bed coating unit (GPCG-5/9) equipped with a bottom spray Wurster coating insert and coated using the solution from Part A at a spray rate of approximately 20 g/minute and a product temperature of approximately 28 to 32° C. The final coating particle contains approximately 20 percent of coating.

Example 7

Preparation of Bi-Layer Tablets Containing Controlled Release Pseudoephedrine, Immediate Release Uncoated Cetirizine Particles and Immediate Release Coated Naproxen Sodium Particles Part A: Blending of Coated Naproxen Particles and Cetirizine Granulation:

Approximately 970.9 g of coated naproxen particles from Example 6, Part B and 194.2 g of cetirizine granulation from Example 2, and 97 g of microcrystalline cellulose (commercially available from the FMC Corporation in Philadelphia, Pa. as Avicel™ pH101) are added to a V-Blender and blended end-over-end for approximately 10 minutes. Approximately 9.6 grams of magnesium stearate is added to the blend and blended end-over-end for approximately 2 minutes.

Part B: Compression of Bi-Layer Tablets:

The pseudoephedrine blend from Example 3 and the blended coated naproxen particles and cetirizine granulation blend from Example 7, Part A are used to compress bi-layer tablets. The tablets are compressed using 0.350×0.710 inches, oval, Standard concave tooling at a compression forces of approximately 20 KN using a KORSCH XL400 rotary tablet press.

TABLE 7

Components of Tablet

| Ingredients | Percent (w/w) | mg/tab |
| --- | --- | --- |
| Controlled Release Pseudoephedrine | 36.41 | 300.0 |
| Coated Naproxen Particles | 48.54 | 400.0 |
| Cetirizine Granulation | 9.71 | 80.0 |
| Microcrystalline Cellulose (Avicel ™ PH 101) | 4.85 | 40.0 |
| Magnesium Stearate | 0.48 | 4.0 |
| TOTAL | 100.0 | 824.0 |

Example 8

Outer Coating of Bi-Layer Tablets

Part A: Preparation of Hypromellose Coating Solution:

A hypromellose based polymer solution (commercially available from the Colorcon Corporation in West Point, Pa. as Opadry® Clear YS-5-7042) is prepared by adding 400 g of hypromellose to 3600 g of purified water in a suitable stainless steel vessel while mixing at 100 RPM. The polymer is allowed to hydrate and the foam to dissipate (approximately 30 minutes).

Part B: Application of Hypromellose Coating Solution to Bi-Layer Tablets:

Approximately 200 g of the bi-layer tablets from Example 5, Part B are added to a Vector Coater tablet coater (commercially available from the Vector Corporation in Marion, Iowa). They are coated using approximately 200 g of solution from Example 8, Part A at a spray rate of approximately 5-10 g/minute and a product temperature of 45° C. to a 2-4 percent weight gain. The final tablet includes approximately 16.5 mg/tablet of coating materials (approximately 2.0 percent of the total tablet weight).

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A tablet comprising a first drug layer and a second drug layer, wherein:
   (i) said first drug layer comprises first drug particles comprising naproxen and third drug particles comprising cetirizine, where said first drug particles and/or said third drug particles are coated with an immediate release coating; and
   (ii) said second drug layer comprising pseudoephedrine, wherein said second drug layer is a sustained release layer adapted to deliver a therapeutically effective amount of pseudoephedrine for a period of at least twelve hours.

2. A tablet of claim 1, wherein said third drug particles are coated with an immediate release coating.

3. A tablet of claim 1, wherein said tablet comprises from about 200 to about 250 mg of naproxen sodium, said tablet comprises from about 100 to about 150 mg of pseudoephedrine HCl, and said tablet comprises from about 4 to about 6 mg of cetirizine dihydrochloride.

4. A tablet of claim 2, wherein said tablet comprises from about 200 to about 250 mg of naproxen sodium, said tablet comprises from about 100 to about 150 mg of pseudoephedrine HCl, and said tablet comprises from about 4 to about 6 mg of cetirizine dihydrochloride.

5. A tablet of claim 1, wherein said second drug layer comprises hypromellose.

6. A tablet of claim 2, wherein said second drug layer comprises hypromellose.

7. A tablet of claim 3, wherein said second drug layer comprises hypromellose.

8. A tablet of claim 4, wherein said second drug layer comprises hypromellose.

9. A tablet of claim 1, wherein said tablet further comprises an outer coating comprising a water-soluble film-forming polymer.

10. A tablet of claim 1, wherein the amount of p-chlorobenzophenone present in the tablet is less than 0.2%, by weight, of the amount of cetirizine in the tablet following storage of the tablet at 40 degrees Celsius and 75 percent relative humidity for at least 3 months.

11. A method of manufacturing a tablet of claim 1, wherein said method comprises:
  (i) preparing said first drug particles comprising naproxen utilizing a granulation process;
  (ii) preparing a second powder mixture comprising pseudoephedrine utilizing a dry blending or granulation process;
  (iii) preparing said third drug particles comprising cetirizine utilizing a layering or granulation process;
  (iv) coating said first drug particles and/or said third drug particles with an immediate release coating;
  (v) blending said first drug particles and said second drug particles to form a first drug blend;
  (vi) compressing said first drug blend to form said first drug layer; and
  (vii) compressing said first drug layer and said second drug particles to form said tablet.

12. A method of claim 11, wherein said third drug particles are coated with said immediate release coating.

13. A method of claim 11, wherein said tablet comprises from about 200 to about 250 mg of naproxen sodium, said tablet comprises from about 100 to about 150 mg of pseudoephedrine HCl, and said tablet comprises from about 4 to about 6 mg of cetirizine dihydrochloride.

14. A method of claim 11, wherein said second drug layer comprises hypromellose.

15. A method of claim 11, wherein said method further comprises spray coating said tablet with a coating solution comprising a water-soluble film-forming polymer.

16. A method of claim 11, wherein the amount of p-chlorobenzophenone present in the tablet is less than 0.2%, by weight, of the amount of cetirizine in the tablet following storage of the tablet at 40 degrees Celsius and 75 percent relative humidity for at least 3 months.

17. A method of treating symptoms of upper respiratory allergies, nasal congestion, and headache, said method comprising administering a tablet of claim 1 to a person in need to such treatment.

18. A method of claim 17, wherein said third drug particles are coated with an immediate release coating.

19. A method of claim 18, wherein said tablet comprises from about 200 to about 250 mg of naproxen sodium; said tablet comprises from about 100 to about 150 mg of pseudoephedrine HCl, and said tablet comprises from about 4 to about 6 mg of cetirizine dihydrochloride.

20. A tablet comprising a first drug particles comprising naproxen, second drug particles comprising pseudoephedrine, and third drug particles comprising cetirizine, wherein (i) said first drug particles and/or said third drug particles are coated with an immediate release coating and (ii) said second drug particles are adapted to deliver a therapeutically effective amount of pseudoephedrine for a period of at least twelve hours.

* * * * *